(12) United States Patent
Lenoir

(10) Patent No.: US 7,452,079 B1
(45) Date of Patent: *Nov. 18, 2008

(54) SYSTEM AND METHOD FOR INDUCING AND MEASURING A CONSENSUAL PUPILLARY RESPONSE

(76) Inventor: Andrew Lenoir, 8390 SW. 106th St., Miami, FL (US) 33156

( * ) Notice: Subject to any disclaimer, the term of this patent is extended or adjusted under 35 U.S.C. 154(b) by 0 days.

This patent is subject to a terminal disclaimer.

(21) Appl. No.: 11/787,223

(22) Filed: Apr. 13, 2007

Related U.S. Application Data

(63) Continuation of application No. 10/683,521, filed on Oct. 10, 2003, now Pat. No. 7,204,590.

(51) Int. Cl.
*A61B 3/10* (2006.01)

(52) U.S. Cl. .......... 351/205; 351/213; 351/221; 351/246

(58) Field of Classification Search .......... 351/205
See application file for complete search history.

(56) References Cited

U.S. PATENT DOCUMENTS

| | | | |
|---|---|---|---|
| 3,450,466 A | 6/1969 | Streisinger | |
| 3,533,683 A | 10/1970 | Stark et al. | |
| 3,551,052 A | 12/1970 | Reiber | |
| 3,777,738 A | 12/1973 | Sugita et al. | |
| 4,012,128 A | 3/1977 | Regan | |
| 4,253,470 A * | 3/1981 | Sheingorn | 600/558 |
| 4,279,478 A | 7/1981 | Matsumura | |
| 4,285,580 A | 8/1981 | Murr | |
| 4,329,737 A | 5/1982 | Triller et al. | |
| 4,765,731 A | 8/1988 | Williams | |
| 4,844,607 A | 7/1989 | Andera et al. | |
| 4,850,691 A | 7/1989 | Gardner et al. | |
| 5,070,883 A | 12/1991 | Kasahara | |
| 5,141,305 A | 8/1992 | Young | |
| 5,187,506 A | 2/1993 | Carter | |
| 5,297,559 A | 3/1994 | Severns | |
| 5,331,358 A | 7/1994 | Schurle et al. | |
| 5,486,880 A * | 1/1996 | House | 351/158 |

(Continued)

OTHER PUBLICATIONS

Abstracts (34) from the 22nd Pupil Colloquium. Point Clear, Alabama. Sep. 1997; www.jiscmail.ac.uk/files/PUPIL/col22abs.htm; Sep. 28, 2001.

(Continued)

*Primary Examiner*—Jessica T Stultz
(74) *Attorney, Agent, or Firm*—Malloy & Malloy, P.A.

(57) ABSTRACT

A system and method allow for inducing and measuring a consensual pupillary response of a subject. The system includes an induction device and a measuring device, the induction device being structured to generate at least one stimuli and to expose a primary eye of the subject to the stimuli. The measuring device of the system includes a monitoring mechanism structured to allow a consensual pupillary response to be detected, and an analysis mechanism to interpret the detected consensual pupillary response. The measuring device may also include a recording device and a display device, to allow recording and displaying of the detected consensual pupillary response, respectively. The method includes exposing the primary eye of the subject to the stimuli, monitoring and detecting the consensual pupillary response in the secondary eye of the subject, and analyzing the detected consensual pupillary response. The method may also include recording and displaying the detected consensual pupillary response.

20 Claims, 4 Drawing Sheets

U.S. PATENT DOCUMENTS

| | | | |
|---|---|---|---|
| 5,490,098 A | 2/1996 | Kardon | |
| 5,638,150 A | 6/1997 | Doherty | |
| 5,767,942 A | 6/1998 | Doherty | |
| 5,784,145 A | 7/1998 | Ghodse et al. | |
| 5,883,691 A | 3/1999 | Ishikawa et al. | |
| 5,989,194 A | 11/1999 | Davenport et al. | |
| 6,022,109 A | 2/2000 | Dal Santo | |
| 6,024,707 A * | 2/2000 | Scinto et al. | 600/558 |
| 6,082,858 A | 7/2000 | Grace et al. | |
| 6,099,185 A | 8/2000 | Huang et al. | |
| 6,170,960 B1 | 1/2001 | Maglica | |
| 6,199,985 B1 | 3/2001 | Anderson | |
| 6,382,792 B1 * | 5/2002 | Khoury | 351/205 |
| 6,416,481 B2 | 7/2002 | Faubert et al. | |
| 6,439,734 B1 | 8/2002 | Lo | |
| 6,616,277 B1 | 9/2003 | Davenport | |
| 6,820,979 B1 | 11/2004 | Stark et al. | |
| 7,204,590 B1 | 4/2007 | Lenoir | |

OTHER PUBLICATIONS

"The influence of iris color on the pupillary light reflex", Bergamin et al.; Graefes Arch Clin Exp Ophthalmol Aug. 1998;236(8):567-70 (ISSN: 0721-832X), 1 page (Abstract only).

Abstracts (31) from the 23rd Pupil Colloquium, Nottingham, England, Aug. 1999; www.jiscmail.ac.uk/files/PUPIL/absbook.htm; Sep. 28, 2001.

Abstracts (34) from the Pacific 24th Pupil Colloquium. Monterey Peninsula, California, Sep. 2001. www.jiscmail.ac.uk/files/pupil/24thcolloquium.htm; Sep. 28, 2001.

Takeda et al., Pupil Control Related MEG, 2001. The Thomson Corporation, Society for Neuroscience vol. 27, 1075.

"Can Color Deficiency Be Detected Through Observing the Consensual Pupillary Response to Different Wavelengths of Light?"Lenoir;Gulliver Preparatory School,Miami,FL;Dec. 2002.

* cited by examiner

SYSTEM AND METHOD FOR INDUCING AND MEASURING A CONSENSUAL PUPILLARY RESPONSE

CLAIM OF PRIORITY

The present patent application is a continuation of previously filed, U.S. patent application filed on Oct. 10, 2003, and having Ser. No. 10/683,521, now U.S. Pat. No. 7,204,590, which is incorporated herein by reference.

BACKGROUND OF THE INVENTION

1. Field of the Invention

The present invention is directed to a system and a method for inducing and measuring a pupillary response, and in particular, a consensual pupillary response in a human subject. The system includes an induction device structured to generate and expose one eye of the subject to a stimuli. The induction device may also include a stimuli adjustment assembly and/or a stimuli control assembly. The system also comprises a measuring device having a monitoring mechanism, and may also include a recording mechanism, a display mechanism, and/or an analysis mechanism. The method of the present invention includes exposing a primary eye of a subject to at least one stimuli, monitoring a secondary eye of the subject and detecting a consensual pupillary response, and analyzing the detected consensual pupillary response.

2. Description of the Related Art

A variety of devices, systems, and associated methodologies have been developed for use in the diagnosis of vision, and in particular, the vision of human subjects. Some of the devices, systems, and methods which have been developed require the active participation of the subject, wherein the subject must be able to comprehend and respond to various visual stimuli presented to them, while other devices, systems, and methods are based upon involuntary responses of the subject to various other stimuli.

Among the most common type of visual diagnostic tool is the simple eye chart which the subject views from a predetermined distance and identifies the various letters and/or numbers which are typically presented on the chart in a series of rows which successively decrease in size from top to bottom. Of course, diagnosis with this tool requires the active participation of the subject in as much as the subject must comprehend and be able to communicate the identity of the various letters and/or numbers presented on the chart. As such, this diagnostic tool has little or no value for infants, small children, or other persons who are unable to comprehend the procedure or to communicate their response.

A similar type of visual diagnostic tool is utilized to test persons for various types of color perception deficiencies, a condition commonly known as color-blindness. There are three main types of color perception deficiencies, each resulting from the loss or malfunction of one of the three types of cones, L-cones, M-cones, or S-cones, which are the portions of the eye which are sensitive to the various wavelengths of light. More in particular, protanopia is the loss of sensitivity to red, and is caused by the malfunction of the L-cones; deuteranopia is the loss of sensitivity to green, and results from the malfunction of the M-cones; and, tritanopia is the loss of sensitivity to blue resulting from the malfunction of the S-cones.

Color-blindness may either be congenital, or it may be acquired, such as, for example, as a side effect of certain pharmacological compositions. One such composition, Ethambutol, an affordable, easily administered, and effective treatment for mycobacterial infections such as tuberculosis and mycobacterium avium intracellularae, which is a common condition in HIV and AIDS patients, cites a decrease in visual acuity as a known side effect, however, it is also noted that the side effect usually subsides if use is promptly discontinued. As a result of this potential side effect, Ethambutol is not normally provided to infants or small children due to the inability to effectively test them for color-blindness to determine if and when use should be discontinued. As such, infants and small children are typically subjected to alternate treatments which generally are more expensive, difficult to administer, often requiring numerous injections rather than oral administration, like Ethambutol, and which may ultimately be a less effective treatment regimen.

Specifically, the typical visual diagnostic tool utilized to test a subject for color-blindness consists of a number, a letter, or a geometric shape being represented by a series of dots of a first color within a field of dots of a second color. Persons with normal color perception are able to discern the pattern of the letter, number, or geometric shape, however, persons with one or more color perception deficiencies may not be able to detect the number, letter, or geometric shape. It is understood, however, that such a diagnostic tool requires the active participation of the person being tested to identify whether or not they see a number, letter, or geometric shape, and to communicate the identity of the number, letter, or geometric shape to the person conducting the test, and is not an effective tool for the diagnosis of infants or small children.

A variety of other devices have been developed to test for color-blindness, such as matching a test color to a reference color, or actuation of a response device when a color change is detected on an output device. Each of these devices once again requires the active participation of the subject whose vision is being tested and, as such, they may not be effectively utilized on subjects who are unable to comprehend the procedural requirements, or to communicate the appropriate responses, including infants and small children.

As indicated above, various other devices, systems, and methods have been developed to allow diagnosis of various parameters of a person's vision which rely upon involuntary reaction of the subject to one or more stimuli. One such device utilizes an infrared light source directed at one pupil of the subject, the subject being otherwise shielded from exposure to visible light. An infrared camera is directed towards the pupil to record the response of the pupil to one or more intermittent visible light stimuli that are projected onto a screen which is positioned within the subject's line of sight. Based upon the response of the pupil, one can presumably diagnose an abnormality in the subject's retina corresponding to the response to the one or more visible light stimuli. While this device does not require the active participation of the subject, as the response of the pupil to the visible light stimuli is involuntary, the device does require specialized, and potentially expensive, infrared camera equipment to capture the response of the pupil to the visible light stimuli and to display the response on a television monitor.

Another method and apparatus provides for exposing one eye of the subject to a visible stimuli and recording the response of the pupil of that eye to evaluate phasic-type neuronal activity. Such phasic-type neuronal activity may result from changes in the visible stimuli such as a change in color and/or luminance. One eye of the subject is covered, such as with an eye patch, while the other eye is tested. Thus, the stimuli and the recording device must both be trained on the same eye of the subject, thereby allowing for incident visible light or other stimuli to reach the eye being tested, potentially producing errors in the results obtained. This method and device do not provide any means for evaluating tonic-type neuronal activity in a subject.

One other method and apparatus has been developed for determining the parameters of a pupillary response in a subject such as, latency, time of constriction, and speed of constriction, following exposure to a visible light stimuli. This method and apparatus again rely upon the use of infrared irradiation of the subject's eye, and measurement of the amount of infrared radiation reflected from the subject's eye both before and after exposure to a visible light stimuli. While this invention may be utilized to indirectly measure the parameters of the various pupillary responses indicated above, neither the method nor the apparatus are directed towards diagnosis of any specific physical condition which may affect the subject's vision.

As such, it would be beneficial to provide a system and associated methodology to test specific parameters of a person's vision, such as color perception deficiencies, which does not require the active participation of the subject. It would also be helpful to provide a system comprising standard components so as to be cost effective, thereby permitting widespread usage among persons requiring such vision testing. Further, it would be beneficial for such a system and method to permit detection and measurement of a consensual pupillary response in one eye of the subject upon exposure of the other eye to a stimuli, such that the exposed eye may be completely isolated from all incident stimuli, to minimize potential error in the results obtained. Additionally, it would be helpful for such a system and method to employ a stimuli control assembly, so as to assure consistency in the stimuli generated, once again, to minimize potential error in the results obtained.

SUMMARY OF THE INVENTION

As indicated above, the present invention comprises a system for inducing and measuring a consensual pupillary response in a subject. The system includes an induction device and a measuring device, wherein the induction device is structured to generate at least one stimuli. In addition, the induction device is structured to expose a primary eye of the subject to at least one stimuli during a test cycle. One embodiment of the present invention includes a test cycle comprising exposure of the primary eye to a plurality of stimuli. The stimuli is structured to induce a consensual pupillary response in a secondary eye of the subject as a result of exposure of the primary eye to the stimuli during the test cycle. At least one embodiment of the present invention includes a light source as the stimuli.

In addition, the induction device of the present invention may comprise a stimuli adjustment assembly structured to permit variation of at least one parameter of the stimuli. In one embodiment, the stimuli adjustment assembly is disposed in an operative position between the light source and the eye of the subject being tested. More in particular, in this embodiment, the stimuli adjustment assembly includes a filter assembly, wherein the filter assembly comprises a plurality of filters structured to allow transmittance of a different one of a plurality of visible light wavelength ranges generated by the light source such as, by way of example only, the visible light wavelength ranges that correspond to the visible "blue light," the visible "red light," and the visible "green light" portions of the electromagnetic spectrum.

One embodiment of the present invention includes an induction device which also comprises a stimuli control assembly. The stimuli control assembly is structured to maintain at least one parameter of the stimuli in a control range.

The stimuli control assembly of the present invention may include, but is not limited to, a power supply having a voltage regulator so as to permit the operator of the system to control the output of the power supply within a predetermined control range.

The system of the present invention also includes a measuring device, as indicated above. The measuring device comprises a monitoring mechanism structured to permit detection of the consensual pupillary response in the secondary eye of the subject. In one embodiment, the measuring device also comprises a recording mechanism communicatively associating with the monitoring mechanism and being structured to at least temporarily preserve the detected consensual pupillary response.

The measuring device of the present invention may also include a display mechanism disposed in communicative association with the monitoring mechanism and structured to permit observation of the detected consensual pupillary response. In yet one further embodiment, the measuring device may comprise an analysis mechanism communicatively interconnected to the monitoring mechanism. This analysis mechanism being structured to interpret the detected consensual pupillary response, where the detected consensual pupillary response is indicative of at least one deficiency in the subject's vision, such as, by way of example, a color perception deficiency.

Also, as indicated above, the present invention comprises a method for inducing and measuring a consensual pupillary response in a subject. Specifically, the method of the present invention includes exposing a primary eye of the subject to at least one stimuli, and monitoring and detecting at least one consensual pupillary response in a secondary eye of the subject. In at least one embodiment, the method may also include recording and/or displaying the detected consensual pupillary response. One further embodiment of the present method further comprises analyzing the detected consensual pupillary response.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
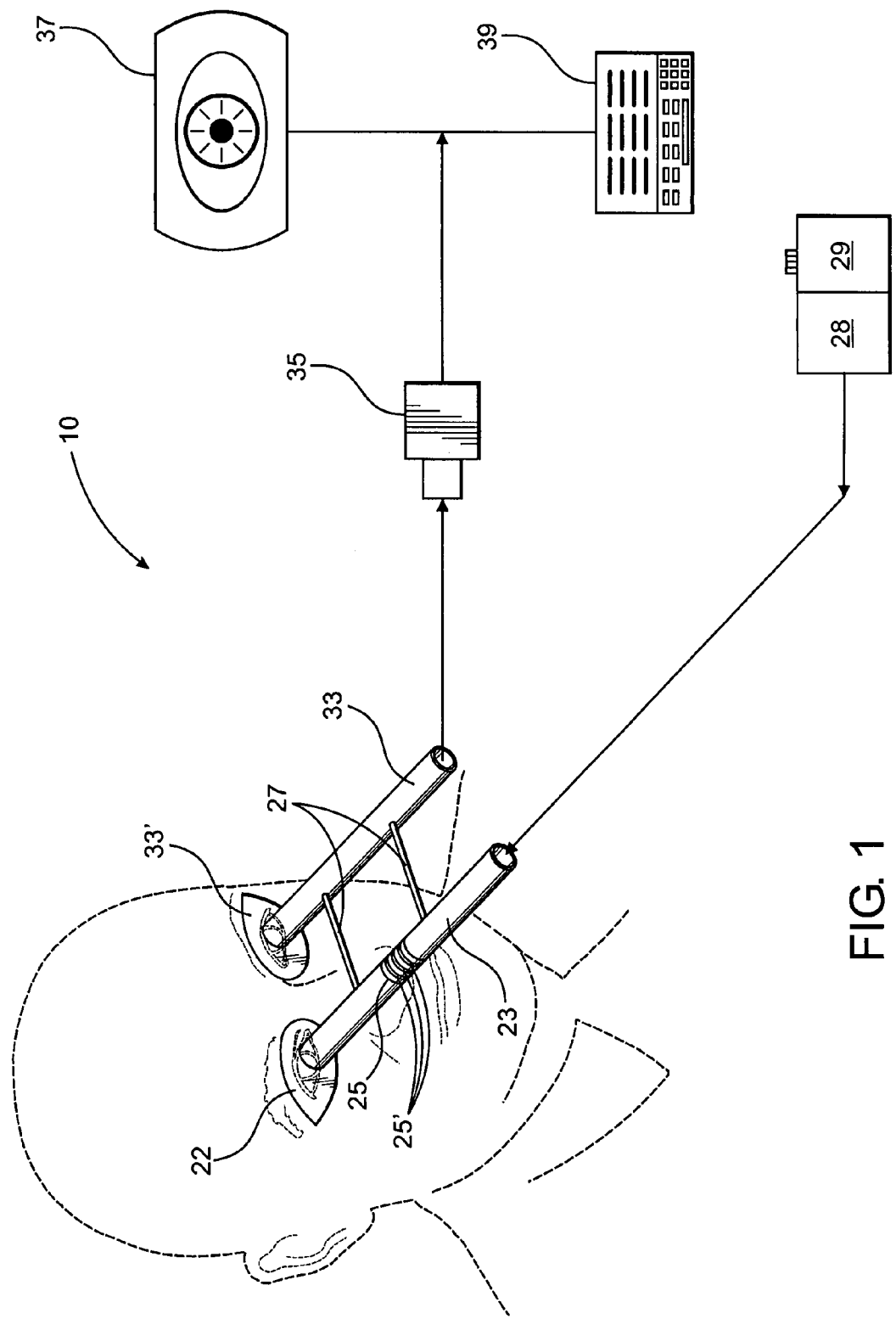
FIG. 1 is a perspective view of one preferred embodiment of the system of the present invention.

The present invention is directed to a system, generally shown as 10, and a method, generally shown as 100, for inducing and measuring a pupillary response in a subject. More in particular, the present invention is directed to a system 10 and a method 100 for inducing and measuring a consensual pupillary response in a secondary eye (SE) of the subject upon exposure of a primary eye (PE) to at least one stimuli 21, during a test cycle. The primary eye (PE) and the secondary eye (SE) may be alternated in a subsequent test cycle (i.e. the right eye of the subject may be the primary eye (PE) in one test cycle, then, the right eye may be the secondary eye (SE) in one other test cycle), however, in at least one embodiment, the dominant eye of the subject is determined, and the dominant eye is designated as the primary eye (PE).

The system 10 of the present invention includes an induction device, generally shown as 20, and a measuring device, generally shown as 30. The induction device 20 of the present invention is structured to generate at least one stimuli 21, and to expose the primary eye (PE) of the subject to the at least one stimuli 21, during the test cycle. More specifically, the induction device 20 is structured to be disposed in an exposing orientation such that the primary eye (PE) may be exposed to the at least one stimuli 21 generated by the induction device 20. In one preferred embodiment of the present invention, the induction device 20 is structured to generate a plurality of stimuli 21, and to alternately expose the primary eye (PE) of the subject to each of the plurality of stimuli 21, during the test cycle. One preferred embodiment of the induction device 20 comprises an eyepiece 22, which is structured to minimize exposure of the primary eye (PE) of the subject to incident stimulation while the induction device 20 is disposed in the exposing orientation.

In at least one embodiment of the present invention, the stimuli 21 comprises a light source 23. The light source 23 is structured to provide a source of "white light," which may comprise the stimuli 21 to the primary eye (PE) of the subject, such that the pupil of the primary eye (PE) constricts upon exposure to the stimuli 21. The mechanism of consensual pupillary response produces a corresponding constriction of the pupil of the secondary eye (SE) in response to the stimulation of the primary eye (PE), wherein the degree of constriction of the primary eye (PE) and the secondary eye (SE) are essentially equal.

The "white light" of the present invention actually comprises a plurality of visible colored light portions each of which is at least partially defined by a distinct visible light frequency or wavelength, more commonly, however, they are defined by a distinct range of visible light wavelengths along the electromagnetic spectrum, wherein the range of visible light wavelengths for "white light" is generally between approximately 400 and 700 nanometers (nm). In addition, a visible "blue light" portion of the electromagnetic spectrum comprises a visible light wavelength range of approximately 400 to 500 nm, a visible "green light" portion of the electromagnetic spectrum comprises a visible light wavelength range of approximately 500 to 600 nm, and a visible "red light" portion of the electromagnetic spectrum comprises a visible light wavelength range of approximately 600 to 700 nm. The non-visible portions of the electromagnetic spectrum comprise ultra-violet light at wavelengths below approximately 400 nm, and infrared light at wavelengths above approximately 700 nm.

One preferred embodiment of the present invention comprises a standard krypton lamp as the light source 23, at least in part due to the fact that krypton lamps do not emit radiation in the ultra-violet wavelength range, thereby preventing the exposure of the subject to the potentially damaging effects of such ultra-violet radiation. In addition, the krypton lamp provides a stable source of visible light which reduces the potential error in the results obtained utilizing the system 10 of the present invention.

At least one embodiment of the induction device 20 of the present invention comprises a stimuli adjustment assembly 24 disposed in an operative position between the source of the stimuli 21 and the primary eye (PE) of the subject. The stimuli adjustment assembly 24 is structured to permit variation of at least one parameter of the stimuli 21 prior to exposure of the primary eye (PE) of the subject to the stimuli. In an embodiment comprising a light source 23 as the stimuli 21, the parameters which may be variable include, but are not limited to, the visible light wavelength range transmitted to the primary eye (PE), the intensity of the visible light transmitted to the primary eye (PE), or the time of exposure of the primary eye (PE) to the stimuli 21, just to name a few.

In one preferred embodiment of the present invention, the stimuli adjustment assembly 24 comprises a filter assembly 25 disposed in an operative position between the source of the stimuli 21 and the primary eye (PE) of the subject. As indicated above, one preferred embodiment comprises a light source 23 as the stimuli 21 and, as such, the filter assembly 25 is disposed between the light source 23 and primary eye (PE) when in an operative position. The filter assembly 25, in at least one embodiment, comprises a plurality of standard filters 25' structured to be disposed in the operative position in the filter assembly 25, either individually or in any one of a variety of combinations as may be required to generate the desired stimuli 21. The plurality of filters 25' may include, but are not limited to, an infrared filter structured to minimize the transmittance of infrared radiation to the subject, a blue, green, and/or red filter such as, for example, standard Kodak Wratten filters, each being structured to transmit essentially only one of the corresponding visible light wavelength ranges, as described above, and one or more neutral density filters structured to permit variation of the transmittance of the light source 23 through the filter assembly 25. As will be appreciated, variation of the combination of the plurality of filters 25 disposed in the operative position in the filter assembly 25 allows the induction mechanism 20 of the present invention to generate and expose the primary eye (PE) of the subject to each of the plurality of visible light wavelength ranges described above, either individually or in any combination.

The induction device 20 of the present invention may also comprise a stimuli control assembly 26, structured to maintain at least one parameter of the stimuli 21 within a control range during the test cycle. In one preferred embodiment, the stimuli control assembly 26 comprises a power supply 28 for the light source 23. In addition, the stimuli control assembly 26 of this preferred embodiment comprises a voltage regulator 29 structured to maintain the output of the power supply 28 within a predetermined voltage control range, thereby facilitating control of the stimuli 21 generated by the light source 23, and specifically, the instantaneous power output of the light source 23. Thus, the stimuli control assembly 26 provides assurance that the instantaneous power output of the light source 23 is not a variable which may introduce error into the results obtained utilizing the system 10 of the present invention. In at least one embodiment of the present invention, the predetermined voltage control range is generally from approximately 2.25 to 2.35 volts.

In at least one embodiment, the one or more neutral density filters may serve as a stimuli control assembly 26. In this embodiment, the neutral density filter or filters are disposed in the operative position in the filter assembly 25 in combination with one of the blue, green, or red filters, and/or the infrared filter. Specifically, the neutral density filter or filters are structured to allow control of the transmittance of the light source 23 through the various combinations of the plurality of filters 25' within a predetermined control range. Once again, the stimuli control assembly 26 provides assurance that the transmittance of the light source 23 is not a variable which may introduce error into the results obtained utilizing the system 10 of the present invention. In at least one embodiment of the present invention, the predetermined control range of the transmittance of the light source 23 is generally between about 3E-07 and 5E-07 watts/centimeter2 (W/cm2) and in one preferred embodiment, the transmittance of the light source 23 is approximately 4E-07 W/cm2.

In one other embodiment, the stimuli control assembly 26 may comprise a standard timer such that the duration of exposure of the primary eye (PE) of the subject to the stimuli 21 may be maintained within a predetermined range such as, by way of example only, between approximately ten and twenty seconds. In this embodiment, the stimuli control assembly 26 assures that the total power output of the light source 23 is not a variable which may introduce error into the results obtained utilizing the system 10 of the present invention.

Figure 3A:
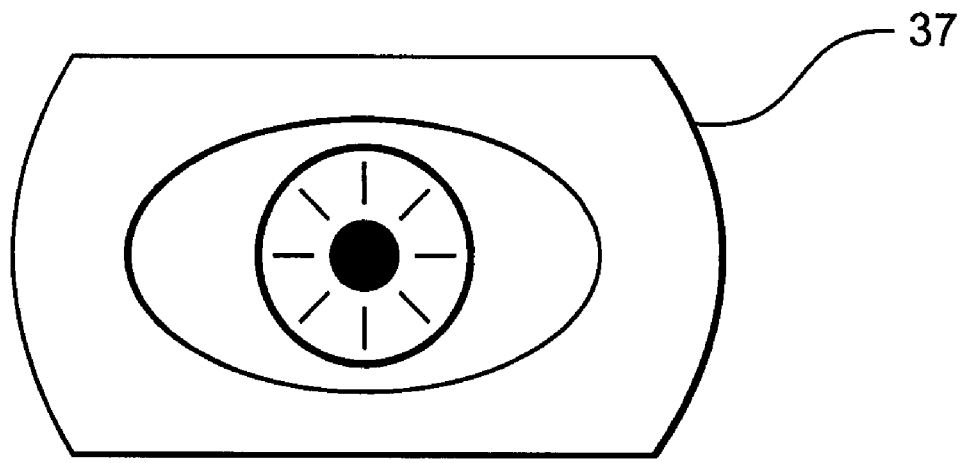
FIG. 3A is an elevation of the display mechanism of FIG. 1 illustrating an example of a secondary eye (SE) of a subject prior to exposure of a primary eye (PE) to a stimuli.
Figure 3B:
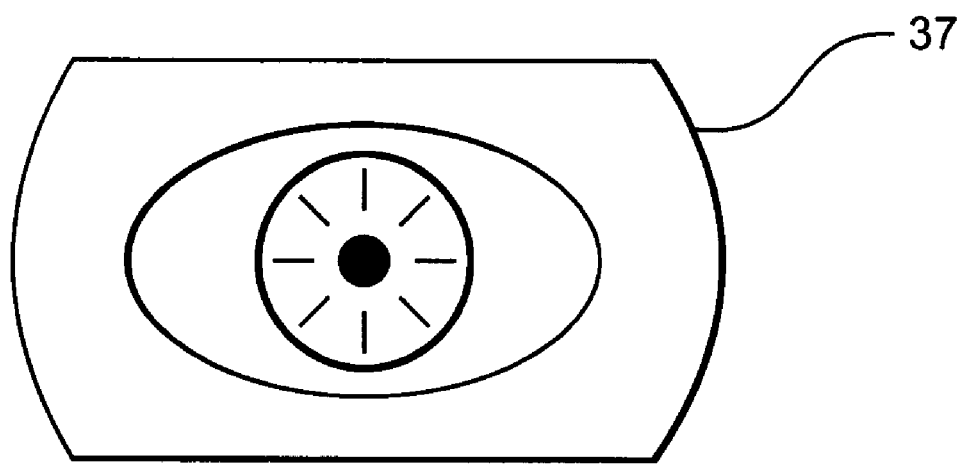
FIG. 3B is an elevation of the secondary eye (SE) of FIG. 3A during exposure of the primary eye (PE) to the stimuli.
Figure 4:
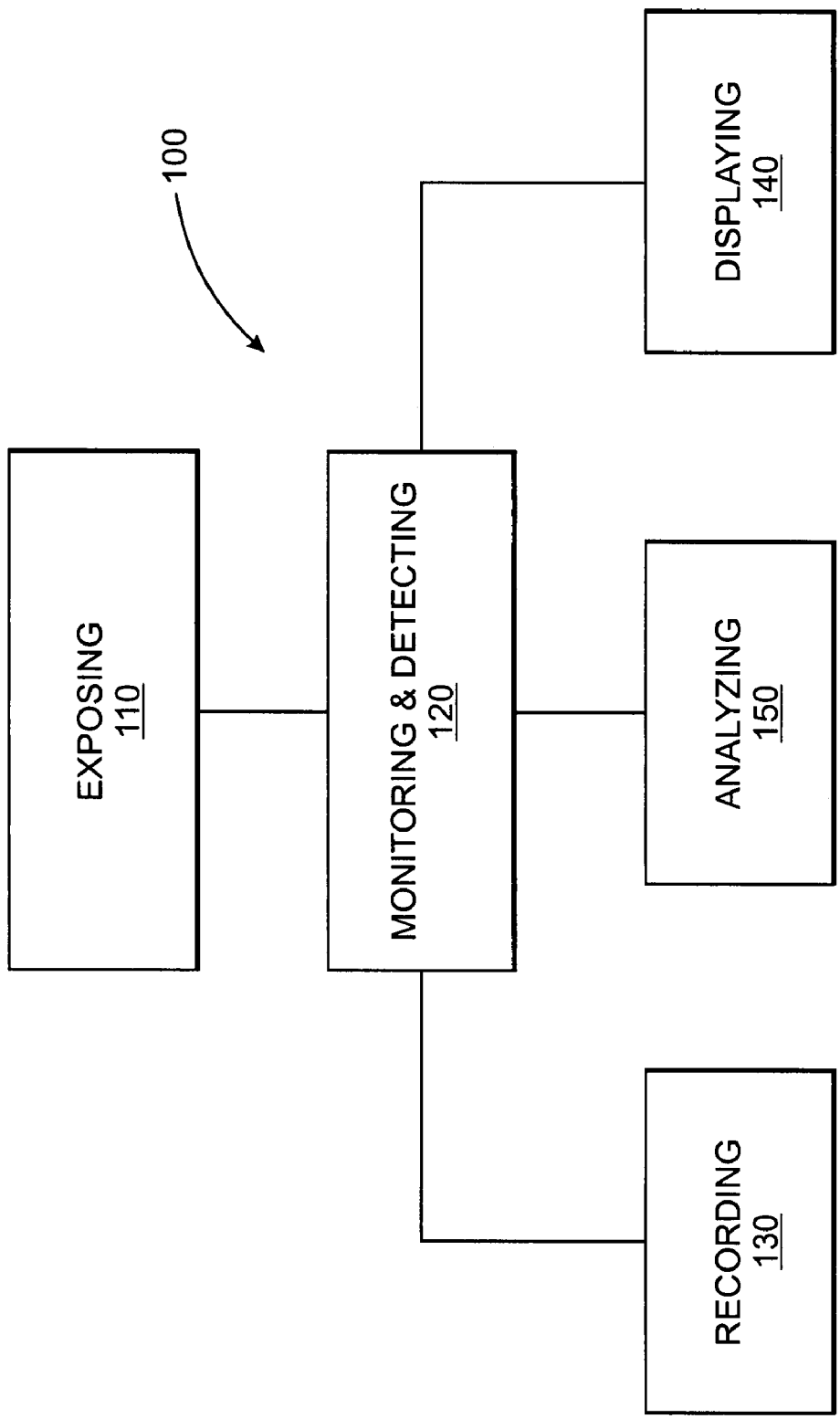
FIG. 4 is a schematic representation of one preferred method of the present invention.

The system 10 of the present invention also includes a measuring device 30, as indicated above. The measuring device 30 comprises at least a monitoring mechanism 32 which is structured to permit detection of a consensual pupillary response in the secondary eye (SE) of the subject as a result of exposure of the primary eye (PE) to at least one stimuli 21 during a test cycle. In particular, in one preferred embodiment, the monitoring mechanism 32 is structured to permit detection of the degree of constriction of the pupil of the secondary eye (SE), both before and during exposure of the primary eye (PE) of the subject to the stimuli 21. FIG. 3A provides an exemplary illustration of the secondary eye (SE) prior to exposure of the primary eye (PE) of the subject to the stimuli 21, while FIG. 3B provides an exemplary illustration of the secondary eye (SE) during exposure of the primary eye (PE) to the stimuli 21.

As such, the monitoring mechanism 32 of the present invention, in one preferred embodiment, comprises a low light imaging apparatus 33 disposed in a monitoring orientation relative to the secondary eye (SE) of the subject, as illustrated in FIG. 1, wherein the monitoring orientation is at least partially defined by the monitoring mechanism 32 being positioned so as to permit the consensual pupillary response of the secondary eye (SE) of the subject to be detected. More specifically, the low light imaging apparatus 33 permits observation of the secondary eye (SE) of the subject to permit at least the diameter of the pupil to be detected, both before and during exposure of the primary eye (PE) of the subject to the stimuli 21.

In one preferred embodiment, while the low light imaging apparatus 33 is disposed in the monitoring orientation relative to the secondary eye (SE) of the subject, the low light imaging apparatus 33 permits viewing of the secondary eye (SE) while shielding the secondary eye (SE) from incident stimulation. In this preferred embodiment, the low light imaging apparatus 33 comprises an eyepiece 33' which, as shown in FIG. 1, is structured to minimize incident stimulation of the secondary eye (SE) of the subject. A low level monitor light source may also be mounted to eyepiece 33' to provide a controlled source of low level irradiation to the secondary eye (SE) of the subject to permit monitoring thereof by the low light imaging apparatus 33. In one preferred embodiment, the low level monitor light source comprises a light emitting diode structured to emit non-visible radiation having a wavelength of approximately 940 nm. It will be appreciated that in this embodiment, the system 10 of the present invention may be set up in at least subdued lighting, thereby facilitating ease of operation.

Figure 2:
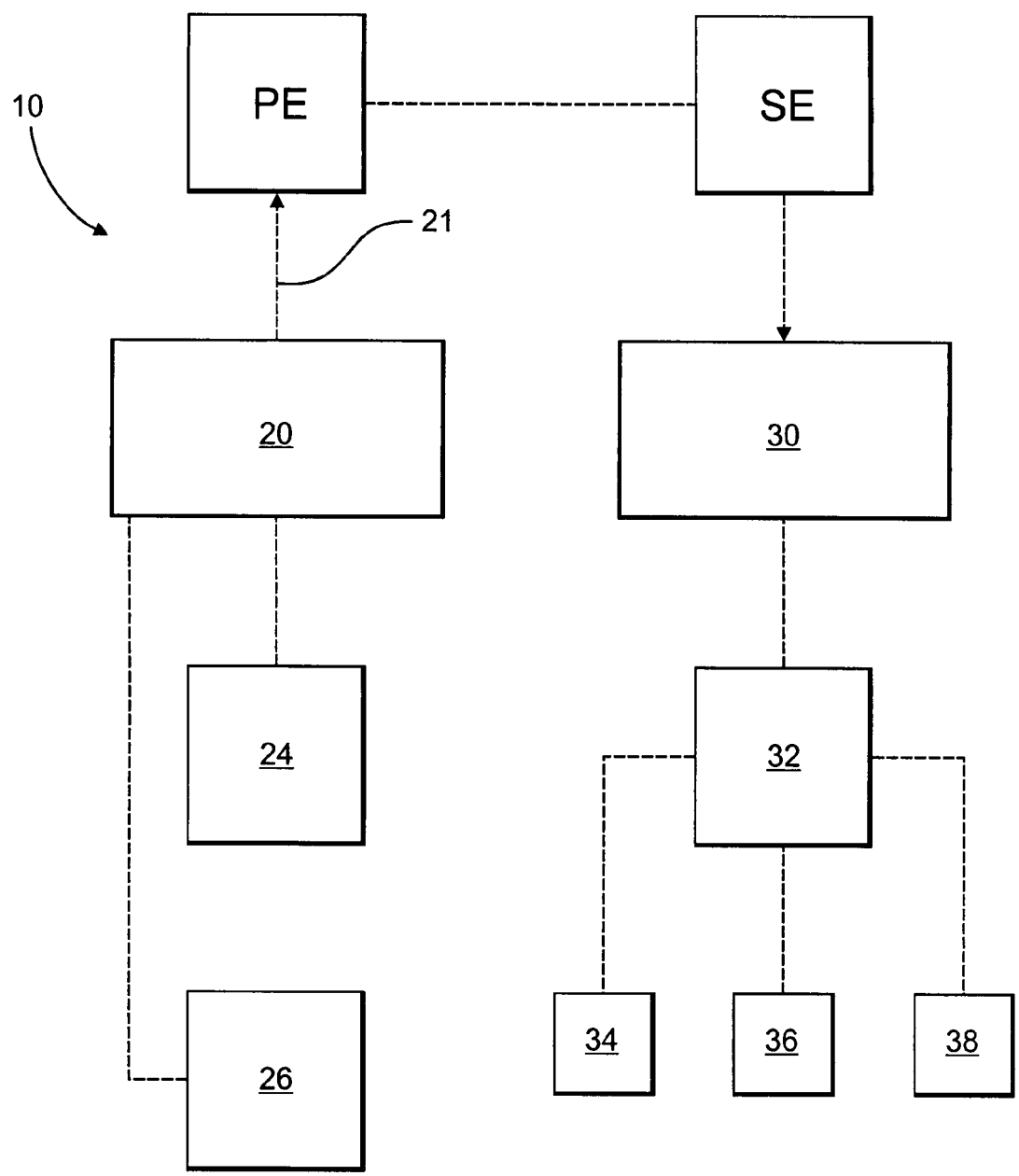
FIG. 2 is a schematic representation of the embodiment of the system of FIG. 1.

Also, as illustrated in FIGS. 1 and 2, one preferred embodiment of the system 10 includes the induction device 20 being attached to the monitoring mechanism 32 by spacers 27, so as to facilitate positioning of the induction device 20 in the exposing orientation relative to the primary eye (PE) of the subject, while at the same time facilitating the positioning of the monitoring mechanism 32 in the monitoring orientation relative to the secondary eye (SE) of the subject.

The measuring device 30 of the present invention may also include a recording mechanism 34 communicatively associating with the monitoring mechanism 32. The recording mechanism 34 is structured to at least temporarily preserve the consensual pupillary response detected by the monitoring mechanism 32. More in particular, the communicative association is at least partially defined by the recording mechanism 34 disposed in an image acquiring configuration relative to the monitoring mechanism 32, wherein the recording mechanism 34 comprises a camera 35 structured and disposed to capture an image of the consensual pupillary response detected by the monitoring mechanism 32, and to at least temporarily preserve the captured image for subsequent retrieval and observation. In one preferred embodiment, the camera 35 is a digital camera allowing one or more discreet images of the consensual pupillary response detected by the monitoring mechanism 32 to be captured during the test cycle. In yet one further preferred embodiment, the camera 35 of the present invention comprises a digital video camera, thereby allowing a plurality of continuous images of the consensual pupillary response detected by the monitoring mechanism 32 to be captured during the test cycle.

In at least one embodiment, the measuring device 30 of the present invention further comprises a display mechanism 36 disposed in communicative association with the monitoring mechanism 32 and being structured to permit observation of the consensual pupillary response detected by the monitoring mechanism 32, as illustrated in FIGS. 3A and 3B. The display mechanism 36 may comprise any standard monitor 37 structured to permit an image to be displayed for viewing, such as a television monitor, a computer monitor, or the monitor in a laptop computer, just to name a few. In one preferred embodiment, the measuring device 30 of the present invention comprises the display mechanism 36 and the recording mechanism 34. This preferred embodiment allows the operator of the system 10 to review the consensual pupillary responses of the subject during one or more test cycles, thereby facilitating an analysis of the same, as discussed in further detail below.

The measuring device 30 of the present invention may further comprise an analysis mechanism 38 which, in at least one embodiment, is communicatively interconnected to the monitoring mechanism 32 and is structured to interpret the at least one, and preferably, the plurality of consensual pupillary responses detected in the secondary eye (SE) of the subject during a test cycle. More in particular, the analysis mechanism 38 is structured to review the one or more detected consensual pupillary responses for an indication of at least one deficiency in the subject's vision. In at least one embodiment, the analysis mechanism 38 of the present invention comprises a personal computer 39 including customized computational software.

In a preferred embodiment, the analysis mechanism 38 is structured to review the plurality of detected consensual pupillary responses for an indication of a color perception deficiency in the subject's vision. Specifically, a plurality of consensual pupillary responses are detected in the secondary eye (SE) of the subject each corresponding to exposure of the primary eye (PE) of the subject to a different one of a plurality of stimuli 21, while the stimuli control assembly 26 assures that the transmittance of the light source 23 is maintained within the predetermined control range of generally between about 3E-07 and 5E-07 W/cm2, preferably, approximately 4E-07 W/cm2, wherein the plurality of stimuli 21 comprise a different one of each of the visible light wavelength ranges (i.e. visible "white light," visible "blue light," visible "green light," and visible "red light").

In this preferred embodiment, the analysis mechanism 38 is structured to determine the relative degree of each of the plurality of consensual pupillary responses such as, for example, by determining the percent of constriction of the pupil of the secondary eye (SE) of the subject corresponding to the exposure of the primary eye (PE) to each of the plurality of stimuli 21.

However, in a subject having a color perception deficiency, for example, protanopia, a red color perception deficiency, the percent of constriction observed upon exposure of the primary eye (PE) of the subject to the visible "red light" stimuli 21, will be significantly less than that observed for each of the other plurality of visible light stimuli 21. Similarly, in a subject exhibiting deuteranopia, a green color perception deficiency, the percent of constriction observed upon exposure to the visible "green light" stimuli 21 will be reduced, and in a subject exhibiting signs of tritanopia, a blue color perception deficiency, the percent of constriction observed upon exposure to the visible "blue light" stimuli 21 will be reduced.

Thus, the system 10 of the present invention may be utilized to diagnose a subject for one or more vision deficiency without the active participation of the subject, via detection, measurement, and analysis of one or more consensual pupillary response of the subject corresponding to one or more stimuli 21. More in particular, the system of the present invention may be utilized to diagnose a subject for a color perception deficiency without the active participation of the subject.

The present invention, as noted above, is also directed to a method, generally shown as 100, for inducing and measuring a pupillary response in a subject and, in particular, for inducing and measuring a consensual pupillary response in a secondary eye (SE) of the subject as a result of exposing a primary eye (PE) to at least one stimuli 21.

Specifically, the method 100 of the present invention comprises exposing 110 the primary eye (PE) of the subject to at least one stimuli 21 during a test cycle, however, one preferred embodiment of the present invention includes exposing 110 the primary eye (PE) of the subject to a plurality of stimuli 21. At least one further embodiment of the method 10 of the present invention includes exposing 110 the primary eye (PE) of the subject to a plurality of visible light wavelength ranges during the test cycle.

Additionally, the method 100 of the present invention comprises monitoring and detecting 120 at least one consensual pupillary response in a secondary eye (SE) of the subject, wherein the consensual pupillary response is a result of exposing 110 the primary eye (PE) to the stimuli 21. One preferred embodiment of the present method 100 comprises monitoring and detecting 120 a plurality of consensual pupillary responses in the secondary eye (SE), wherein each of the plurality of detected consensual pupillary responses corresponds to a different one of each of a plurality of stimuli 21, such as, by way of example only, a different one of a plurality of visible light wavelength ranges.

At least one embodiment of the method 100 of the present invention also comprises recording 130 the at least one detected consensual pupillary response, however, a preferred embodiment of the method comprises recording 130 the plurality of detected consensual pupillary responses. In addition, the method 100 of the present invention may comprise displaying 140 the at least one consensual pupillary response, and, once again, preferably, displaying 140 each of the plurality of detected consensual pupillary responses.

The method 100 of the present invention further comprises analyzing 150 the at least one detected consensual pupillary response. More in particular, the method 100 of the present invention includes analyzing 150 the at least one detected consensual pupillary response for an indication of a deficiency in the subject's vision.

A most preferred embodiment of the method 100 of the present invention comprises analyzing 150 each of the plurality of detected consensual pupillary responses, and in particular, analyzing each of the plurality of detected consensual pupillary responses for an indication of a color perception deficiency in the subject's vision.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A system for inducing and measuring a consensual pupillary response in a subject comprising:
- an induction device structured to generate at least one stimuli,
- said at least one stimuli comprising a light source structured to transmit a visible light portion of an electromagnetic spectrum, said visible light portion comprising visible light wavelengths from about 400 to 700 nanometers,
- said induction device further structured to expose a primary eye of the subject to said at least one stimuli during a test cycle,
- said induction device also structured to shield the secondary eye of the subject from incident visible light stimulation during said test cycle,
- said at least one stimuli structured to induce a consensual pupillary response in a secondary eye of the subject as a result of said exposure of the primary eye to said at least one stimuli during said test cycle,
- said induction device comprising a stimuli adjustment assembly structured to permit variation of at least one parameter of said at least one stimuli,
- said at least one parameter comprising a preselected range of said visible light wavelengths, wherein each said preselected range of said visible light wavelengths corresponds to one of a plurality of visible colored light portions of said electromagnetic spectrum,
- said stimuli adjustment assembly disposed in an operative position between said stimuli and the primary eye of the subject and being structured to substantially limit transmittance of said visible light portion to said preselected range of said visible light wavelengths corresponding to one of said plurality of visible colored light portions,
- said induction device further comprising a stimuli control assembly structured to maintain at least one parameter of said at least one stimuli in a predetermined control range, and a monitoring mechanism structured to permit detection of said consensual pupillary response, wherein said detected consensual pupillary response is at least partially defined by a constriction of the pupil of the secondary eye in response to said exposure of the primary eye to said at least one stimuli, wherein a degree of constriction of the pupil of the secondary eye is substantially equal to a degree of constriction of the pupil of the primary eye.

2. The system as recited in claim 1 wherein said detected consensual pupillary response is indicative of at least one deficiency in the subject's vision.

3. The system as recited in claim 2 wherein said at least one deficiency comprises a color perception deficiency.

4. The system as recited in claim 1 wherein said stimuli adjustment assembly comprises a filter assembly.

5. The system as recited in claim 1 wherein said stimuli control assembly comprises a voltage regulator structured to maintain a voltage supply to said induction device within a predetermined control range.

6. A system for inducing and measuring a consensual pupillary response in a subject comprising:
    an induction device structured to generate at least one stimuli,
    said induction device further structured to expose a primary eye of the subject to said at least one stimuli during a test cycle,
    said at least one stimuli structured to induce a consensual pupillary response in a secondary eye of the subject as a result of said exposure of the primary eye to said at least one stimuli during said test cycle,
    said at least one stimuli comprising a light source structured to transmit a plurality of visible light wavelengths ranging from about 400 to 700 nanometers,
    said induction device comprising a stimuli adjustment assembly structured to permit variation of at least one parameter of said at least one stimuli, said at least one parameter comprising a plurality of preselected ranges of said visible light wavelengths each corresponding to one of a plurality of visible colored light portions,
    said induction device further comprising a stimuli control assembly structured to maintain at least one parameter of said at least one stimuli in a corresponding predetermined control range,
    a monitoring mechanism structured to permit detection of said consensual pupillary response,
    said detected consensual pupillary response at least partially defined by a constriction of the pupil of the secondary eye in response to said exposure of the primary eye to said at least one stimuli, wherein a degree of constriction of the pupil of the secondary eye is substantially equal to a degree of constriction of the pupil of the primary eye, and
    said detected consensual pupillary response is indicative of a color perception deficiency in the subject's vision.

7. The system as recited in claim 6 wherein said light source comprises a krypton lamp structured to transmit said plurality of visible light wavelengths.

8. The system as recited in claim 7 wherein said krypton lamp is further structured not to emit ultra-violet radiation.

9. The system as recited in claim 8 wherein said stimuli adjustment assembly is disposed in an operative position between said light source and the primary eye of the subject.

10. The system as recited in claim 9 wherein said stimuli adjustment assembly comprises a plurality of filters, each of said plurality of filters structured to substantially limit transmittance to one of said plurality of preselected ranges of said visible light wavelengths.

11. The system as recited in claim 6 wherein said stimuli control assembly comprises a plurality of neutral density filters.

12. The system as recited in claim 11 wherein said at least one parameter comprises a transmittance of said light source, and said plurality of neutral density filters are structured to maintain said transmittance of said light source within a corresponding predetermined control range.

13. The system as recited in claim 12 wherein said corresponding predetermined control range comprises a transmittance of said light source of between about 3E-07 to 5E-07 watts per centimeter$^2$.

14. The system as recited in claim 13 wherein at least one other parameter comprises a duration of exposure, and said stimuli control assembly further comprising a timer structured to maintain said duration of exposure within a corresponding predetermined control range.

15. The system as recited in claim 6 wherein said stimuli control assembly comprises a timer structured to maintain a duration of exposure of said primary eye to said light source within a corresponding predetermined control range.

16. The system as recited in claim 15 wherein said predetermined control range comprises a duration of exposure of between about ten to twenty seconds.

17. A method for inducing and measuring a consensual pupillary response in a subject comprising:
    exposing a primary eye of the subject to at least one stimuli with an induction device to induce a consensual pupillary response in a secondary eye of the subject during a test cycle, wherein the consensual pupillary response is at least partially defined by a constriction of the pupil of the secondary eye in response to exposure of the primary eye to the at least one stimuli and a degree of constriction of the pupil of the secondary eye is substantially equal to a degree of constriction of the pupil of the primary eye,
    shielding the secondary eye from incident stimuli during the test cycle,
    varying at least one parameter of the stimuli prior to the test cycle via a stimuli adjustment assembly,
    maintaining at least one parameter of the stimuli in a predetermined control range during the test cycle via a stimuli control assembly,
    shielding the primary eye from incident stimuli during the test cycle,
    monitoring the secondary eye of the subject and detecting the consensual pupillary response, and
    analyzing the detected consensual pupillary response for an indication of at least one deficiency in the subject's vision.

18. The method as recited in claim 17 further comprising analyzing the detected consensual pupillary response for an indication of a color perception deficiency in the subject's vision.

19. The method as recited in claim 17 further comprising exposing the primary eye of the subject to a plurality of stimuli with the induction device during a test cycle.

20. The method as recited in claim 19 further comprising detecting each of a plurality of consensual pupillary responses in the secondary eye of the subject each corresponding to a different one of the plurality of stimuli.

* * * * *